US005709797A

United States Patent [19]
Bocchiola et al.

[11] Patent Number: 5,709,797
[45] Date of Patent: Jan. 20, 1998

[54] METHOD OF ISOLATING CYCLOSPORINS

[75] Inventors: Gianettore Bocchiola, Magherno; Vittorio Buran, Corsico; Ambrogio Magni, Osnago, all of Italy

[73] Assignee: Poli Industria Chimica S.p.A., Milan, Italy

[21] Appl. No.: 658,731

[22] Filed: Jun. 5, 1996

[51] Int. Cl.$^6$ .................................. B01D 15/08
[52] U.S. Cl. .................. 210/635; 210/656; 530/317; 530/321; 530/413
[58] Field of Search ................ 530/317, 321, 530/413, 417; 210/635, 656, 659, 198.2, 502.1

[56] References Cited

U.S. PATENT DOCUMENTS

| | | | |
|---|---|---|---|
| 4,108,985 | 8/1978 | Rüegger et al. | 424/177 |
| 4,117,118 | 9/1978 | Härri et al. | 424/177 |
| 4,215,199 | 7/1980 | Härri et al. | 435/71 |
| 4,396,542 | 8/1983 | Wenger | 260/112.5 |
| 4,456,592 | 6/1984 | Okumura | 530/317 |
| 4,554,351 | 11/1985 | Wegner | 544/177 |
| 4,764,503 | 8/1988 | Wegner | 514/11 |
| 4,868,285 | 9/1989 | Wall | 530/317 |
| 4,908,434 | 3/1990 | Mertelsmann | 530/413 |
| 5,079,341 | 1/1992 | Galphin et al. | 530/321 |
| 5,116,816 | 5/1992 | Dreyfuss et al. | 514/11 |
| 5,156,960 | 10/1992 | Bokány et al. | 435/71.1 |
| 5,202,310 | 4/1993 | Levy et al. | 514/11 |
| 5,256,547 | 10/1993 | Rudat et al. | 435/71.1 |
| 5,271,935 | 12/1993 | Franco et al. | 424/115 |
| 5,284,826 | 2/1994 | Eberle | 514/11 |
| 5,350,574 | 9/1994 | Erlanger et al. | 514/9 |
| 5,382,655 | 1/1995 | Szánya et al. | 530/317 |
| 5,409,816 | 4/1995 | Lundell et al. | 435/713 |
| 5,447,854 | 9/1995 | Goto et al. | 435/71.3 |

FOREIGN PATENT DOCUMENTS

| | | | |
|---|---|---|---|
| 2108655 | 10/1993 | Canada | 530/317 |
| WO 96/12031 | 4/1996 | WIPO | 530/317 |
| WO 96/12032 | 4/1996 | WIPO | 530/317 |

OTHER PUBLICATIONS

C. E. Isaac et al.; *Production of Cyclosporins by Tolypocladium Niveum Strains*, Antimicrobial Agentx and Chemotherapy 34, No. 1:121–127 (1990).

Skoog; *Liquid Chromatography, Principals of Instrumental Analysis* 3rd. Ed. 696–702 (1985).

*Primary Examiner*—Ernest G. Therkorn
*Attorney, Agent, or Firm*—Townsend and Townsend and Crew LLP

[57] ABSTRACT

The present invention provides a method for isolating cyclosporin by adsorption chromatography. The method comprises the steps of: (a) loading a crude solution containing a cyclosporin onto adsorption chromatography column containing an adsorption resin, (b) eluting the cyclosporin from the adsorption chromatography column, and (c) collecting the eluted cyclosporin. The step of eluting the cyclosporin is carried out by passing an eluting solvent through the column, which comprises a hydrophilic component and a lipophilic component, wherein the cyclosporin is separately eluted from other compounds by providing a hydrophilic/lipophilic balance in the eluting solvent that selectively desorbs the cyclosporin from the column.

42 Claims, No Drawings

METHOD OF ISOLATING CYCLOSPORINS

FIELD OF THE INVENTION

The present invention relates to methods for producing, and recovering cyclosporins. More particularly, the invention relates to chromatographic methods of isolating and purifying cyclosporins.

BACKGROUND OF THE INVENTION

Cyclosporins are a group of non-polar cyclic oligopeptide compounds having immunosuppressant activity, which are produced by fungal fermentation. Cyclosporins have been employed for several years to combat rejection of transplanted organs and tissues in humans. Recently, investigators have been seeking additional therapeutic applications for the drug.

At least nine different cyclosporins are produced by fungi, including cyclosporin A, B, C, D, E, F, G, H, and I, all having varying amino acid composition. Cyclosporin A is the major component and currently enjoys the most widespread clinical use. See, e.g., Ruegger et al., *Helv. Chim. Acta* 59:1075 (1976); Traber et al., *Helv. Chim. Acta* 60:1568 (1977); Rehacek and De-xiu, *Process Biochem* 26:157 (1991). Cyclosporin A is commercially available under the tradename SANDIMMUNE® from Sandoz Corp.

Cyclosporins were originally isolated as metabolites produced by fungal strains of *Cylindrocarpon lucidum* Booth and *Tolypocladium inflatum* Gams, isolated from soil samples from the United States of America and Norway. *T. inflatum* is also known as *Tolypocladium niveum*. Isaac et al., *Antimicro. Agents Chemother.* 34:121 (1990). (The genus *Tolypocladium* was first described by Gams, *Persoonia*, 612:185 (1971); the genus name *Beauveria* has been used synonymously with *Tolypocladium*.) Species of *Tolypocladium* are typically slow in growth and form white, flocculent colonies with a large amount of spores.

A production strain of *Tolypocladium* (*Tolypocladium inflatum* (NRRL 8044)) was at first identified as *Trichoderma polysporum* (Link ex Pers) Rifai. The use of this strain for the production of antibiotic substances is described in Finnish Patent No. 54606. Growth conditions and taxonomy of this production strain are provided in Dreyfuss et al., *Eur. J. Appl. Microbiol.* 3:125 (1976).

Other cyclosporin producing strains are described in Finnish Patent No. 52851 (*Cylindrocarpon lucidum* Booth (NRRL 5760)), German patent 298276 (*Tolypocladium inflatum* strain SF 136), Great Britain patent 2,227,489 (*Tolypocladium varium*), Japan patent 826 3093 (two strains of cyclosporin producing *Fusarium*), and U.S. Pat. No. 5,409,816 (*Tolypocladium* sp. LEA3CBS 630.92). However, not all strains of *Tolypocladium* species are cyclosporin producing. Isaac et al. (1990).

The industrial fermentation of cyclosporin-producing fungi species is carried out in submersed cultures and yields cyclosporin product containing microorganisms which must be separated from fermentation broths by filtration. Thereafter, the cells are opened using chemical, mechanical, or thermic lysis. The individual cyclosporin products must then be separated from their closely related derivatives and metabolites. Typically, individual cyclosporins may be recovered by chromatographic separation, followed by purification.

Conventionally known chromatographic methods of separating cyclosporins involve partition or ion exchange chromatography. Partition chromatography separates the individual cyclosporin products from the mixture by utilizing the partition coefficient between the stationary phase and the mobile phase of eluting solvent. Ion exchange chromatography effects the separation of cyclosporins by chemically binding the ionic groups of the individual compound to be immobilized on the counterions present on the surface of the ion exchange resin. Because of the nature of the chemical structure of cyclosporins, partition chromatography is the preferred means of separation. For example, U.S. Pat. No. 4,108,985 to Rüegger et al., U.S. Pat. No. 4,117,118 to Härri et al., U.S. Pat. No. 5,256,547 to Rudat et al., and U.S. Pat. No. 5,409,816 to Lundell et al., each describe the separation of cyclosporins by partition chromatography utilizing a silica gel column, an alumina gel column, or some combination of silica gel and alumina gel columns. The disadvantage of utilizing such mineral gels is that where the mixture contains some amount of water, the columns require lengthy regeneration cycles prior to reuse.

One alternative separation technique which has been explored involves the separation of cyclosporins by supercritical fluid extraction. For example, Canadian Patent No. 2,108,655 discusses the extraction of cyclosporins from fungal mycelia with supercritical carbon dioxide. Economic and industrial scale concerns have limited the commercial application of this method.

Adsorption chromatography has been utilized for several years for the separation of water-soluble compounds. Adsorption chromatography differs from partition and ion exchange chromatography in that it involves adsorption of the compounds to be separation onto the adsorption column and subsequent individual recovery of the adsorbed compounds by passing an organic solvent of suitable polarity through the column. The water-soluble compounds are loaded onto the resin by passing an aqueous solution of the compound through the resin column, whereby the compounds are attracted out of the solution and become adsorbed onto the column. The passage of the organic solvent through the column effects the release of the compound from the column, resulting in the individual elution of the compounds to be separated. As an example, U.S. Pat. No. 5,271,935 to Franco et al. discusses the use of adsorption chromatography for the isolation of cammunocin, a water-soluble peptide. Because adsorption chromatography requires the solubilization of the compounds to be separated in an aqueous phase, it has previously been employed only for the separation of water-soluble compounds, unlike cyclosporins.

There remains a need in the art for efficient, cost-effective methods for the isolation and purification of cyclosporins. There also remains a need in the art for industrially feasible methods for the isolation and purification of cyclosporins. These and other objects are met by the methods of the present invention.

SUMMARY OF THE INVENTION

The present invention provides the distinct advantage that the same solvent may be employed for the entire process, from the cellular lysis through the chromatographic isolation of the cyclosporin.

As a first aspect, the present invention provides a method for isolating a cyclosporin by adsorption chromatography. The method comprises the steps of: (a) loading a crude solution containing a mixture of cyclosporin and compounds to be separated therefrom onto an adsorption chromatography column containing an adsorption resin, (b) eluting the cyclosporin from the adsorption chromatography column, and (c) collecting the eluted cyclosporin. The adsorption resin adsorbs both the cyclosporin and the compounds to be separated therefrom. The cyclosporin is separately eluted from the adsorption chromatography column in step (b) by passing through the column, an eluting solvent comprising a hydrophilic component and a lipophilic component, and having a hydrophilic/lipophilic balance which selectively desorbs the cyclosporin from the adsorption resin to provide an eluted cyclosporin essentially free of compounds to be separated therefrom. The hydrophilic/lipophilic balance of the eluting solvent that selectively desorbs the cyclosporin is provided by varying the ratio of the hydrophilic component to the lipophilic component in the eluting solvent during the step of eluting. As used herein, the phrase "essentially free" has its conventional meaning in the art, and refers to the isolated cyclosporin products containing not more than 10% of other compounds.

As a second aspect, the present invention provides a method for isolating a cyclosporin from a mixture containing two or more cyclosporins. The method comprises the steps of: (a) loading a crude solution containing a mixture of at least two cyclosporins onto an adsorption chromatography column containing an adsorption resin, (b) eluting each of the individual cyclosporins from the adsorption chromatography column, and (c) separately collecting each of the eluted individual cyclosporins. The adsorption resin adsorbs each of the cyclosporins thereon during the loading step (a). Each of the cyclosporins are then separately eluted from the column in step (b) by passing therethrough an eluting solvent comprising a hydrophilic component and a lipophilic component, and having a hydrophilic/lipophilic balance which selectively desorbs each of the individual cyclosporins from the adsorption resin. The hydrophilic/lipophilic balance of the eluting solvent that selectively desorbs the cyclosporins is provided by varying the ratio of the hydrophilic component to the lipophilic component in the eluting solvent during the step of eluting.

As a third aspect, the present invention provides a method of extracting cyclosporin from cells containing intracellular cyclosporin. The method comprises contacting the cells to a lysis solution comprising a lysis solvent under conditions sufficient to lyse said cells, and lysing said cells in the lysis solution. The lysis solvent is selected from the group consisting of ketones, ethers, esters, amides, nitriles, and mixtures thereof.

As a fourth aspect, the present invention provides a method of separating cyclosporin from a crude solution containing cyclosporin and cellular debris. The method includes microfiltering the crude solution.

As a fifth aspect, the present invention provides a method for isolating a cyclosporin by adsoprtion chromatography. The method includes the steps of: (a) lysing cells containing intracellular cyclosporin with a lysis solution comprising a lysis solvent to produce lysed cells; (b) microfiltering the lysed cells to separate cellular debris and to produce a crude solution comprising cyclosporin and compounds to be separated therefrom; (c) loading the crude solution onto an adsorption chromatography column containing an adsorption resin that adsorbs both the cyclosporin and the other compounds to be separated therefrom; then (d) eluting the cyclosporin from the adsorption chromatography column by passing an eluting solvent therethrough; and then (e) collecting the eluted cyclosporin. The lysis solvent is a ketone. The loading step comprises introducing onto the adsorption chromatography column, a solution comprising the crude solution and a loading solvent. The eluting solvent comprises a hydrophilic component and a lipophilic component. During the eluting step, the cyclosporin is separately eluted from the other compounds by providing a hydrophilic/lipophilic balance in the eluting solvent that selectively desorbs the cyclosporin from the adsorption resin to provide an eluted cyclosporin essentially free of the other compounds to be separated therefrom. The hydrophilic/lipophilic balance is provided by varying the ratio of the hydrophilic component to the lipophilic component in the eluting solvent during the eluting step. Advantageously, the lysis solvent, the lipophilic phase of the loading solvent and the lipophilic phase of the eluting solvent may all be the same.

As a sixth aspect, the present invention provides another method for isolating a cyclosporin by adsoprtion chromatography. The method comprises the steps of: (a) lysing cells containing intracellular cyclosporin with a lysis solution comprising a lysis solvent to produce lysed cells; (b) microfiltering the lysed cells to separate cellular debris and to produce a crude solution comprising a mixture of at least two different cyclosporins to be separated; (c) loading the crude solution onto an adsorption chromatography column containing an adsorption resin that adsorbs each of the different cyclosporins; then (d) eluting each of the individual cyclosporins from the adsorption chromatography column by passing an eluting solvent therethrough; and then (e) collecting each of the separately eluted individual cyclosporins. The lysis solvent is a ketone. The loading step comprises introducing onto the adsorption chromatography column, a solution comprising the crude solution and a loading solvent. The eluting solvent comprises a hydrophilic component and a lipophilic component. During the eluting step, the individual cyclosporins are separately eluted from the adsorption column by providing a hydrophilic/lipophilic balance in the eluting solvent that selectively desorbs each of the individual cyclosporins from the adsorption resin to provide separately eluted individual cyclosporins essentially free of different cyclosporins. The hydrophilic/lipophilic balance that selectively desorbs the individual cyclosporins is provided by varying the ratio of the hydrophilic component to the lipophilic component in the eluting solvent during the eluting step. Advantageously, the lysis solvent, the lipophilic phase of the loading solvent and the lipophilic phase of the eluting solvent may all be the same.

As a seventh aspect, the present invention provides a method for isolating cyclosporin A from a mixture by adsorption chromatography. The method comprises the steps of: (a) loading a crude solution containing a mixture of cyclosporin A and compounds to be separated therefrom onto an adsorption chromatography column containing an adsorption resin that adsorbs both the cyclosporin A and the compounds to be separated therefrom, (b) separately eluting the cyclosporin A from the adsorption chromatography column by passing therethrough an eluting solvent comprising a hydrophilic component and a lipophilic component, and having a hydrophilic/lipophilic balance which selectively desorbs the cyclosporin A from the adsorption resin, and (c) collecting the eluted cyclosporin A. The process may further include step (d) of purifying the collected cyclosporin A by crystallization to yield substantially pure cyclosporin A powder. The hydrophilic/lipophilic balance is provided during the elution step (b) by varying the ratio of hydrophilic component to the lipophilic component in the eluting solvent from about 50:50 at the initiation of step (b) of eluting the cyclosporin A, to about 20:80 at the end of step (b). The phrase "substantially pure" as used herein refers to cyclosporin having a purity profile in conformity with the United States Pharmacopoeia and supplement. The phrase does not require absolute purity of 100%.

As an eighth aspect, the present invention provides another method of a method for isolating cyclosporin A from a mixture by adsorption chromatography. The method includes the steps of: (a) lysing cells containing intracellular cyclosporin A with a lysis solution comprising acetone to produce lysed cells; (b) microfiltering the lysed cells to separate cellular debris and to produce a crude solution comprising cyclosporin A; (c) loading the crude solution containing cyclosporin A and compounds to be separated therefrom onto an adsorption chromatography column containing a adsorption resin that both adsorbs cyclosporin A and the compounds to be separated therefrom; then (d) separately eluting cyclosporin A from the adsorption chromatography column by passing an eluting solvent therethrough; and then (e) collecting the eluted cyclosporin A. The eluting solvent comprises a hydrophilic and lipophilic phase, and cyclosporin A is separately eluted from the adsorption column by providing a hydrophilic/lipophilic balance in the eluting solvent that selectively desorbs cyclosporin A from the adsorption resin to provide eluted cyclosporin A essentially free of compounds to be separated therefrom. The hydrophilic/lipophilic balance is provided by varying the ratio of the hydrophilic phase to the lipophilic phase in the eluting solvent from about 50:50 at the initiation of step (c) of separately eluting cyclosporin A, to about 20:80 at the end of step (c).

The foregoing and other objects and aspects of the present invention are explained further in the detailed description and examples set forth hereinbelow.

DETAILED DESCRIPTION OF THE INVENTION

The methods of the present invention provide new means of easily and economically isolating cyclosporin from a crude fermentation broth mixture. The methods of the present invention have the distinct advantage of providing a means for efficiently isolating commercially viable quantities of cyclosporin, rapidly and with little waste to column materials, without compromising the purity of the cyclosporins obtained. According to the methods of the present invention, cyclosporin may be isolated from a crude solution containing cyclosporin and other compounds by: (a) loading the crude solution onto an adsorption chromatography column containing an adsorption resin, (b) eluting the cyclosporin from the adsorption chromatography column, and (c) collecting the eluted cyclosporin.

As used herein, the phrase "adsorption chromatography" has its conventional meaning in the art. Adsorption chromatography is a form of high performance liquid chromatography which differs from partition and gel permeation chromatography. In adsorption chromatography, compounds are separated based upon attraction to either the adsorption resin or eluting sovlent. In adsorption chromatography, the compounds to be separated compete with eluting solvent for sites on the surface of the adsorption resin. In the loading phase, the compounds to be separated are loaded onto the column using a solvent which causes the compounds to preferentially adsorb onto the surface of the resin. The compounds are desorbed from the resin, and thereby eluted, by using an eluting solvent having characteristics which cause the solvent to preferentially adsorb on the resin, thus displacing the previously adsorbed compounds to be separated.

As used herein, the phrase "adsorption chromatography column" has its conventional meaning in the art. An adsorption chromatography column is a chromatography column useful for adsorption chromatography and containing an adsorption resin which is capable of adsorbing the compounds to be separated.

The phrase "loading solvent" refers to the solvent mixture employed for loading or charging the mixture containing the compounds to be separated onto the adsorption chromatography column. The loading solvent must have characteristics which cause the compounds contained within the mixture to be preferentially adsorbed onto the surface of the adsorption resin. Compounds will preferentially adsorb on the adsorption resin if the resin has a stronger attraction for the compounds within the mixture than the solvent which is passing over the resin surface.

The phrase "eluting solvent" (or "mobile phase") has its conventional meaning in the art. The eluting solvent is passed through the column containing the adsorption resin and compounds adsorbed thereon. The characteristics of the eluting solvent cause the separate elution of the compounds from the column, based upon the competing attraction of the adsorbed compounds versus the eluting solvent for the resin adsorption sites. As the characteristics of the eluting solvent change, the adsorbed compounds are separately desorbed from the resin as the eluting solvent becomes more attractive thereto.

Adsorption chromatography has not previously been employed for the separation of cyclosporins because it generally is not well suited for the separation of compounds which are similar in structure. The inventors have surprisingly found that cyclosporins may be separated using adsorption chromatography and have further found an unexpected advantage over the partition chromatography techniques conventionally employed for the separation of cyclosporins. More particularly, the inventors have discovered that adsorption chromatography resins are not only capable of efficiently separating cyclosporins, but also do not require the time-consuming and expensive regeneration cycles which are required between separations on partition chromatography columns.

Partition chromatography columns comprise silica or alumina resins, which are easily spoiled by any quantity of water in the loaded sample because of their strong attraction for water. In order to obtain separation of cyclosporin, the water must be removed from the column packing prior to loading the next sample for separation.

The adsorption chromatography resins contained within the adsorption chromatography columns employed in the instant invention are not spoiled by contact with water. In fact, the adsorption chromatography systems employed in the present invention preferably utilize solutions containing aqueous components in the loading solvent and/or eluting solvent. Consequently, the column may be regenerated and ready for reuse after only a brief washing cycle which removes any remaining adsorbed compounds from the resin surface. The wash solution may also comprise an aqueous component.

The adsorption chromatography column employed in the methods of the present invention may be of any suitable length, as will be appreciated by those skilled in the art. Typically, the adsorption column is about 3.75 cm in diameter and about 4 m in length. The adsorption chromatography column contains an adsorption resin, typically a macroreticular adsorption resin. Preferably, the macroreticular adsorption resin is a non-ionic adsorption resin. Suitable macroreticular adsorption resins are well known in the art. Specific examples of suitable adsorption chromatography resins include but are not limited to styrenic, acrylic, methacrylic, and phenolic adsorption resins. One preferred adsorption chromatography resin for use in the methods of the present invention includes a styrenic adsorption resin having divinylbenzene functionalities. Styrenic adsorption chromatography resins having divinylbenzene functionalities are commercially available from Rohm and Haas under the tradename AMBERLITE XAD®, such as XAD4®, XAD16®, XAD1180®, and XAD1600®. Acrylic, methacrylic, and phenolic adsorption resins are also commercially available from Rohm & Haas under the tradenames AMBERLITE XAD7®, IR C50®, and DUOLITE XAD761®, respectively.

In the first step of the inventive method, a crude solution including the cyclosporin to be separated is loaded onto the resin packed column. The crude solution containing cyclosporin is typically a crude solution obtained from the fermentation of microorganisms which are capable of producing cyclosporin. Several methods of producing cyclosporins are known and include those described in U.S. Pat. No. 4,117,118 to Harri, the disclosure of which is incorporated herein by reference in its entirety. During fermentation, the microorganisms produce cyclosporin which is accumulated inside the microorganisms and which can be crudely extracted from the microorganisms by lysis and filtration using conventional lysis and filtration techniques.

Utilizing conventional lysis and filtration techniques, the microorganisms obtained at the end of the fermentation process are typically washed with water to eliminate fermentation residues which are filtered away. Thereafter, the biomass is subjected to mechanical, physical or chemicophysical lysis. Mechanical lysis can be achieved by crushing cells by treating an aqueous or aqueous-organic solvent suspension of the cells with a powerfull stirrer such as TURRAX®. Physical lysis utilize pressure shock or ultrasound to break the cell wall and achieve lysis. These techniques are not applicable in large scale production because the cost and equipment involved are prohibitive. Physico-chemical lysis is achieved by treating the cells or biomass with acidic or basic substances at different temperatures depending upon the stability and solubility of the product to be isolated. Alternatively, an organic solvent can be utilized under conditions known to those skilled in the art to break the cell wall and extract the intracellular product. Physico-chemical lysis utilizing organic solvents such as alkanols (e.g., methanol, ethanol, and isopropanol) is typically the least expensive technique because it does not require specially designed equipment. As is know to those skilled in the art, any type of stirred vessel can be used to run the operation and moreover it can be well coupled with micro filtration according to the techniques of the present invention.

The concentration of the biomass suspension created by cellular lysis may be adjusted by concentration or dilution to obtain a solvent concentration which is appropriate for loading the mixture on the adsorption chromatography column. Preferably, the biomass suspension containing the cyclosporin, fermentation broth, fermentation microorganism residues, lysed cells, and other fermentation compounds, is filtered prior to introduction onto the adsorption column. Any suitable filtration means known to those skilled in the art may be employed. For example, the biomass suspension may be filtered by forcing the biomass suspension through a screen immediately prior to charging the column.

The intracellular cyclosporins may also be extracted from the microorganisms using the lysis and micro filtration techniques of the present invention. According to the methods of the present invention, the intracellular cyclosporin may be extracted from the microorganism cells by contacting the cells to a lysis solution comprising a lysis solvent selected from the group consisting of ketones, ethers, esters, amides, nitriles, mixtures thereof, and mixtures of one or more of these organic solvents with water under conditions sufficient to lyse the cells, and then lysing the cells in the lysis solution. The preferred lysis solvent is a ketone, more preferably acetone.

The amount of lysis solvent needed to lyse the cyclosporin producing cells is between about 0.5 and about 5 l/kg mycellium (containing 75% water), depending upon the particular lysis solvent employed. Preferably, the percentage of lysis solvent which is reacted with the mycelium is not less than about 60%. In the embodiment wherein the lysis solvent is a ketone, the amount of lysis solvent is typically between about 0.5 and about 2 l/kg mycellium. Typically, the lysis solvent is contacted with the cells for between about 1 and about 24 hours. The temperature under which lysis is carried out will depend upon the particular lysis solvent employed but typically ranges between about 25° C. up to the reflux temperature of the lysis solvent. When the lysis solvent is a ketone, preferably lysis is carried out at about 40° C. Preferably, the lysis solvent is contacted with the cells with stirring.

As in the case of utilizing conventional lysis techniques, the concentration of the biomass suspension created by cellular lysis may be adjusted by concentration or dilution to obtain a solvent concentration which is appropriate for loading the mixture on the adsorption chromatography column. In the embodiment wherein the lysis solvent, the lipophilic phase of the loading solvent, and the lipophilic phase of the eluting solvent comprise the same organic solvent, the present invention provides the further advantage that the same solvent may be employed throughout the entire method of isolating cyclosporin, from cellular lysis through collection of the isolated cyclosporin.

It is preferred that the biomass suspension containing the cyclosporin, fermentation broth, fermentation microorganism residues, lysed cells, and other fermentation compounds, is filtered prior to introduction onto the adsorption column. As described above, conventional filtration techniques may be employed. However, the present invention provides a method of separating cyclosporin from a biomass suspension containing cyclosporin and such cellular debris. The method of the present invention comprises microfiltering the biomass suspension produced from cellular lysis. The microfiltration process of the present invention may be carried out using a conventional microfiltration apparatus. Typically, microfiltration employs a filtration media of porosity ranging from about 0.05 to about 1 μm. Microfiltration may be carried out as a batch or continuous process. Batch applications are usually performed in laboratory applications while continuous operations may be preferred for commercially viable processes. Microfiltration membranes are commercially available. Typically, microfiltration membranes fall within the categories of either polymeric membranes or ceramic membranes. Ceramic membranes are currently preferred for commercial applications because of their resistance and stability at high temperatures in a wide variety of pH ranges. Ceramic membranes are useful for tangential filtrations as well.

Utilizing the microfiltration technique, particles can be removed from the biomass liquid phase by convective flow parallel to the membrane. Microfiltration is particularly advantageous in the filtration of cyclosporin producing biomasses because micro filtration techniques resist filtration obstruction. The microfiltration process of the present invention provides the further advantages that the fermentation residues can be removed and the cells can be concentrated on the same microfiltration apparatus, and the solvent concentration can also be adjusted on the same apparatus.

In yet another embodiement of the present invention, the lysis and microfiltration may be carried out by tangential micro filtration. In this embodiment, the harvest broth including the cells containing cyclosproin are filtered in a tangential microfilter, the suspension is continuously recycled in a loop. The wall of the loop comprises a porous material and the suspension may be recycled or the liquid phase may be removed by opening a collection valve. The removal of liquid phase in this manner yields a more concentrated suspension. The continual removal of portions of the liquid phase in this manner produces a thick paste. The solvent may then be loaded into the micro filtration equipment, and recycling is then continued for at least one hour without collecting the permeate. During the course of the process, the cells are lysed. Thereafter, the filtrate containing cyclosporin may be collected. Thus, this embodiment has the advantage that two operations (lysis and microfiltration) may be run using the same equipment.

When utilizing the cellular lysis techniques of the present invention, there is no need to dry the mycellium prior to conducting cellular lysis. This is because the presence of water in the crude solution does not pose any threat to the column packing (i.e., resin). Similarly, the lysis and micro-filtration techniques of the present invention provide the further advantage that the crude fermentation mixture obtained from the lysis and microfiltration of the cyclosporin producing microorganisms may be loaded onto the column without the need for evaporation of the solvents employed in the cellular lysis. This is because the lysis solvent may also be employed as the lipophilic component of the loading and eluting solvents to facilitate the isolation of the cyclosporin.

The crude solution obtained from fermentation, or fermentation broth after cellular lysis may be a mixture of a single cyclosporin and derivatives, microorganism fragments, fermentation by-products, lysed cells, and impurities. As will be known to those skilled in the art, derivatives, fragments, fermentation by-products and impurities include any compound which are present at the termination of a fermentation process normally employed for the production of cyclosporin. The various derivatives, fragments, by-products, and impurities present will depend upon the microbiological species fermented, the fermentation medium, and other factors known to those skilled in the art. In addition, the mixture may contain two or more cyclosporins, which are desireously separated from each other.

The loading step may be carried out using methods well known to those skilled in the art. Typically, the loading step is carried out by introducing onto the adsorption chromatography column, a solution comprising the crude solution which contains cyclosporin, and a loading solvent. The loading solvent typically comprises a hydrophilic component and a lipophilic component, and has a hydrophilic/lipophilic balance such that the cyclosporin preferentially adsorbs onto the adsorption resin. The mixture may be introduced onto the column by pumping a feed stream onto the column using conventional pump and column loading equipment. The loading solvent, which is introduced onto the column concurrently with the crude solution containing cyclosporin, must have a sufficient hydrophilic/lipophilic balance to permit the adsorption of the cyclosporin onto the resin adsorption sites. The proper hydrophilic/lipophilic balance may change based upon the contents of the crude solution to be separated, but is nevertheless readily determinable by those skilled in the art. As will be apparent to those skilled in the art, the hydrophilic/lipophilic balance of the loading solvent may be adjusted by altering the ratio of the hydrophilic component to the lipophilic component. Typically, the loading solvent comprises the hydrophilic component and the lipophilic component in a ratio of between about 90:10 and about 0:100, preferably between about 70:30 and about 0:100, more preferably about 60:40.

The hydrophilic component of the loading solvent comprises aqueous solutions. Aqueous solutions are solutions which consist primarily of water, normally greater than about 90 weight percent water, and can be essentially pure water in certain circumstances. For example, an aqueous solution can be distilled water, tap water, or the like. However, an aqueous solution can include water having substances such as pH buffers, pH adjusters, organic and inorganic salts, sugars, amino acids or surfactants incorporated therein. The solution also can be a co-solvent mixture of water and minor amounts of one or more solvents which are miscible therewith. Preferably, the hydrophilic component of the loading solvent is pure water.

The lipophilic component of the loading solvent may comprise any organic solvent known to those skilled in the art to have the desired lipophilic character. Typically, the lipophilic component is selected from the group consisting of aliphatic alcohols, ketones, ethers, esters, amides, nitriles, and mixtures thereof. Suitable alcohols include but are not limited to methanol, ethanol, isopropanol, and the like. Suitable ketones include but are not limited to acetone, butanone, and the like. Suitable ethers include but are not limited to dioxane, tetrahydrofuran, dioxolane, and the like. Suitable esters include but are not limited to ethyl acetate, and the like. Suitable amides include but are not limited to dimethylformamide, dimethylacetamide, and the like. Suitable nitriles include but are not limited to acetonitrile, and the like. Preferably, the lipophilic component of the loading solvent is selected from the group consisting of acetone, isopropyl alcohol, and acetonitrile.

Once the crude solution containing the cyclosporin mixture is loaded on the column, the cyclosporin is separated from the remaining components of the mixture during the elution step. The cyclosporin is separated from the remaining components adsorbed on the resin by providing a hydrophilic/lipophilic balance in the eluting solvent passing through the column which selectively desorbs the cyclosporin from the adsorption resin. By providing a hydrophilic/lipophilic balance in the eluting solvent which causes the eluting solvent to preferentially adsorb onto the resin, the cyclosporin can be selectively displaced by the eluting solvent and desorbed. Once desorbed the cyclosporin elutes from the column.

The eluting solvent comprises a hydrophilic component and a lipophilic component. The hydrophilic component and the lipophilic component may be any of those described hereinabove in connection with the loading solvent. Thus, a further advantage of the inventive method is that the same solvent components may be employed for the elution of the cyclosporin as are employed for the loading of the crude solution containing the cyclosporin and for the lysis of the cells containing cyclosporin. The preferred eluting solvent comprises water as the hydrophilic component and acetone as the lipophilic component.

The hydrophilic/lipophilic balance of the eluting solvent must be sufficient to desorb or displace the cyclosporin selectively. The hydrophilic/lipophilic balance should not be sufficient to simultaneously desorb or displace all compounds adsorbed onto the resin. The hydrophilic/lipophilic balance necessary for desorption of the adsorbed cyclosporin may be provided by varying the ratio of hydrophilic component to lipophilic component in the eluting solvent. Preferably, the ratio of hydrophilic component to lipophilic component is varied during the course of the elution step, thus resulting in a varying hydrophilic/lipophilic balance in the eluting solvent during the elution step. By varying the hydrophilic/lipophilic balance in the eluting solvent during the elution step, the selective desorption and elution of the cyclosporin is accomplished.

In the embodiment wherein the crude solution contains two or more cyclosporins, a hydrophilic/lipophilic balance is provided so as to selectively desorb each of the cyclosporins individually. Selective desorption of each of the cyclosporins is accomplished by varying the hydrophilic/lipophilic balance of the eluting solvent during the course of the elution step, as described above.

The ratio of the hydrophilic component to the lipophilic component at the initiation of the elution step may be between about 96:4 and about 0:100 inclusive, depending upon the compounds to be separated, and is readily determinable by those skilled in the art. Preferably, the ratio of hydrophilic component to lipophilic component is about 40:60 at the initiation of the elution step. More preferably, the ratio of hydrophilic component to lipophilic component is about 50:50 at the initiation of the elution step.

The ratio of hydrophilic component to lipophilic component at the end of the elution step may be between about 0:100 to about 90:10 inclusive, depending upon the compounds to be separated. In one preferred embodiment, the ratio of hydrophilic component to lipophilic component is about 20:80 at the end of the elution step. In another preferred embodiment, the ratio of hydrophilic component to lipophilic component is about 40:60 at the end of the elution step.

In one preferred embodiment, the ratio of hydrophilic component to lipophilic component is about 40:60 at the initiation of the elution step and about 20:80 at the end of the elution step.

In another preferred embodiment, the ratio of hydrophilic component to lipophilic component is about 50:50 at the initiation of the elution step and about 20:80 at the end of the elution step.

The rate of alteration or variation of the hydrophilic/lipophilic balance is dictated by the rate of elution of the cyclosporin and other compounds in the crude solution, which are to be separated therefrom. The rate of alteration of the hydrophilic/lipophilic balance should be sufficiently slow to permit the distinct separation of the individual adsorbed compounds.

As the individual, separated compounds elute from the column, the cyclosporin may be collected by collecting the fractions of eluant which correspond to the cyclosporin. The proper fractions for collection can be determined based upon the known hydrophilic/lipophilic balance of the eluting solvent at a given time. The known hydrophilic/lipophilic balance of the eluting solvent and the known required characteristics of the eluting solvent for desorption of cyclosporin permit the determination of the eluant corresponding to the cyclosporin or cyclosporins to be collected. In the embodiment wherein the mixture contains at least two cyclosporins for separation, the step of collecting the cyclosporin comprises separately collecting the fractions of eluant which correspond to each of the individual cyclosporins. The proper eluant fractions corresponding to each individual cyclosporin will be readily determinable by those skilled in the art in the same manner as employed for determining the proper eluant for a single cyclosporin.

As will be readily apparent to those skilled in the art, the methods of the present invention may also include additional conventional processing steps. For example, the methods of the present invention may also include the step of purifying the collected cyclosporin by drying and/or crystallizing the cyclosporin so as to obtain substantially pure, powdered cyclosporin. Crystallization techniques for the purification of cyclosporin to yield powdered cyclosporin having a purity in compliance with United States Pharmacopoeia standards are well known to those skilled in the art. Any such conventionally accepted techniques may be employed for the purification of cyclosporin isolated by the methods of the present invention.

The following examples are provided to illustrate the present invention, and should not be construed as limiting thereof. In these examples, "DMF" means dimethylformamide, "THF" means tetrahydrofuran, "kg" means kilograms, "g" means grams, "l" means liters, "ml" means milliliters, "m" means meters, "°C." means degrees Centigrade, "hr" means hours, "min." means minute(s), and "m/min." means meters per minute.

EXAMPLE 1

Cyclosporins are produced using standard fermentation techniques, from the fermentation of *Tolypocladium*.

Upon completion of fermentation, 13 l of fermentation broth known to contain 30 g of cyclosporin A, 8 g of cyclosporin B, and 7.5 g of cyclosporin C are filtered and washed. Approximately 4 kg of wet mycelium having a moisture content of 75% are obtained. Thereafter, the mycelium is treated with 6 l of acetone and allowed to stir overnight. The biomass suspension obtained is filtered, and biomass residues are discarded. The resulting solution is adjusted to approximately 40% water. The adjusted solution is loaded on 2.5 l of adsorbent resin bed XAD1600®. On the loaded resin, an elution is carried out with a water:acetone gradient mixture varying from 50:50 to 25:75, and individual fractions of 250 ml are separately collected.

Cyclosporin C is collected in the first 40 fractions. The next 10 fractions contained cyclosporin B, and cyclosporin A is collected in fractions 70–100. The fractions containing cyclosporin A are collected and concentrated to small volume and a repeated extraction with toluene is carried out. The product is then crystallized with acetone to yield cyclosporin A.

EXAMPLE 2

The separation procedure is carried out according to Example 1 above. The elution fractions containing both cyclosporin A and cyclosporin B, i.e., fractions at 60–70 min. are subjected to another chromatographic separation to separate cyclosporin A and cyclosporin B. The purification is carried out on the same resin bed as employed in Example 1 after a conditioning cycle with the same solvent mixture employed for loading the cyclosporin mixture onto the resin.

The isolation is completed by varying the elution solvent mixture as described in Example 1. The fractions containing cyclosporin A are collected and concentrated to small volume and a repeated extraction with toluene is carried out. The final crystallization with acetone yields cyclosporin A having a purity profile meeting the requirements of the United States Pharmacopoeia and supplement.

EXAMPLE 3

The fermentation and filtration procedures are carried out according to Example 1. Approximately 4 kg of wet mycelium is treated with 6 l isopropyl alcohol and stirred overnight. The concentration of the resulting solution is adjusted with water to achieve an isopropyl alcohol content of about 40%. The adjusted solution is aloaded on 2.5 l of adsorbent resin bed XAD7® (acrylic resin). On the loaded resin, an elution is carreid out with a water:isopropyl alcohol gradient mixture varying from 40:60 to 30:70, and individual fractions of 250 ml are separately collected.

The fractions containing cyclosporin A are concentrated to small volume and extracted with toluene. The product is then crystallized with acetone to yield cyclosporin A.

EXAMPLE 4

The fermentation and filtration procedures are carried out according to Example 1. Approximately 4 kg of wet mycelium is treated with 7 l acetonitrile and stirred overnight. The concentration of the resulting solution is adjusted with water to achieve an organic solvent content of about 55%. The adjusted solution is loaded on 2.5 l of adsorbent resin bed XAD761® (phenolic resin). On the loaded resin, an elution is carreid out with a water:acetonitrile gradient mixture varying from 40:60 to 20:80, and individual fractions are separately collected.

EXAMPLE 5

The fermentation and filtration procedures are carried out according to Example 1. Approximately 4 kg of wet mycelium is treated with 6 l isopropyl alcohol and stirred overnight. The concentration of the resulting solution is adjusted with water to achieve an isopropyl alcohol content of about 40%. The adjusted solution is loaded on 2.5 l of adsorbent resin bed XAD7® (acrylic resin). On the loaded resin, an elution is carreid out according to the conditions described in Example 1, but using a water:isopropyl alcohol gradient mixture varying from 40:60 to 30:70, and individual fractions are separately collected as described in Example 3. The fractions containing cyclosporin A are concentrated to small volume and extracted with toluene. The product is then crystallized with acetone to yield cyclosporin A.

EXAMPLE 6

The fermentation and filtration procedures are carried out according to Example 1. Approximately 4 kg of wet mycelium is treated with 7 l acetonitrile and stirred overnight. The concentration of the resulting solution is adjusted with water to achieve an acetonitrile content of about 55%. The adjusted solution is loaded on 2.5 l of adsorbent resin bed XAD761®(phenolic resin). On the loaded resin, an elution is carreid out according to the condition described in Example 1, but using a water:aceonitrile gradient mixture varying from 40:60 to 20:80. A fraction containing cyclosporin C is collected followed by a mixture of cyclosporins A, B, and C, and then by a faction containing cyclosporin A. The cyclosporin A is recovered and recrystallized according to Example 5.

EXAMPLE 7

The fermentation and filtration procedures are carried out according to Example 1. Approximately 4 kg of wet mycelium is treated with 12 l tetrahydrofuran and stirred for at least 2 hours at 35°–40° C. The suspension is filtered and the filter cake is washed with tetrahydrofuran. The concentration of the resulting solution is adjusted with water to achieve a tetrohydrofuran content of about 60%. The adjusted solution is loaded on to a column containing AMBERLITE XAD1600®. On the loaded resin, an elution is carreid out according to the conditions described in Example 1, but using a water:tetrohydrofuran gradient mixture varying from 50:50 to 30:70. A fraction containing a mixture of cyclosporins C, B, and A is discarded while a fraction containing cyclosporin B and A is collected.

The concentration of the fractions containing cyclosporins B and A is adjusted to achieve a water:tetrohydrofuran ratio of 60:40. The solution is then loaded onto the same adsorption column for a second chromatographic elution which is carried out under the same conditions as the first.

A fraction containing a mixture of cyclosprorins B and A is recycled in successsive chromatography in this manner while a fraction containing cyclosporin A is concentrated in the manner described in Example 5 to recover cyclosporin A product.

EXAMPLE 8

The fermentation and filtration procedures are carried out according to Example 1. Approximately 4 kg of wet mycelium is treated with 3 l dimethylformamide and stirred for about 2 hours at 50° C. The suspension is filtered and the concentration of the resulting solution is adjusted to achieve a water:dimethylformamide ratio of about 70:30. The adjusted solution is loaded onto a column containing XAD1180®. On the loaded resin, an elution is carreid out according to the conditions described in Example 1, but using a water:dimethylformamide gradient mixture varying from 30:70 to 40:60. A fraction containing cyclosporin A and a small amount of cyclosporin B is obtained.

EXAMPLE 9

The fermentation and filtration procedures are carried out according to Example 1. Approximately 4 kg of wet mycelium is treated with 70 l of water containing 4% ethyl acetate under reflux for 5 hours. After cooling at 25° C., the suspension is filtered, and the solution is loaded onto a column containing 2.5 l of XAD761®. On the loaded resin, an elution is carreid out according to the condition described in Example 1, but using water saturated with ethyl acetate as the elution solvent.

EXAMPLE 10

Cyclosporins are produce using standard fermentation techniques, from the fermentation of *Tolypocladium*.

Upon completion of fermentation, 18 l of fermentation broth known to contain 45 g of cyclosporin A, 12 g cyclosporin B, 11 g cyclosporin C are filtered and washed. Approximately 6 kg of wet mycelium having a moisture content of 75% is obtained. Thereafter, the mycelium is treated with 8 l of acetone and allowed to stir overnight. The biomass suspension obtained is filtered, and biomass residues are discarded. The resulting solution is adjusted to approximately 40% water. The adjusted solution is loaded in 4.5 l of adsorbent resin bed XAD 1600® within an adsorption chromatography column having a diameter of 3.75 cm. On the loaded resin, an elution is carried out with 15 l of acetone (50% in water) followed by acetone (60% in water). After the elution of a fraction of about 10 l that doesn't contain cyclosporin products, fractions of 250 ml are collected.

The first 10 fractions collected contain cyclosporin C. The fractions 11-18 contain a mixture of 3 cyclosporins. The fractions 19-100 contain cyclosporin A. During all the steps of the chromatographic process the linear flow rate is about 1 m/min.

The fractions containing cyclosporin A are joined and concentrated to small volume. After concentration, extraction with ethyl acetate is carried out. The final crystallization with acetone yields cyclosporin A.

EXAMPLE 11

The fractions 24-100 of the first chromatography described in Example 10 are subjected to another chromatography to separate cyclosporin A and B. The chromatographic purification is carried out on the same resin bed and under the same conditions employed in Example 10 after a conditioning cycle with the same solvent mixture employed for loading the cyclosporin mixture onto the resin.

The purification is carded out by varying the elution solvent mixture as described in Example 10. Cyclosporin A is obtained having a purity profile meeting the requirements of the United States Pharmacopoeia and supplement.

EXAMPLE 12

Approximately 4 kg of wet mycelium is treated with 6 l isopropyl alcohol and stirred overnight. To the solution obtained water is added to achieve approximately 40% alcohol. The solution is then loaded on 9 l of acrylic resin XAD 7®. On the loaded resin, an elution is carried out with a water:isopropyl alcohol gradient mixture varying from 60:40 to 40:60, and individual fractions of 250 ml are collected.

Cyclosporin C is collected in the first fractions. The next fractions contained a mixture of cyclosporins C and B. Thereafter, a mixture of cyclosporins B and A is collected followed by cyclosporin A in the last part of the elution. The last fractions are concentrated to small volume and extracted with ethyl acetate. The final crystallization with acetone yields cyclosporin A.

EXAMPLE 13

Approximately 4 kg of wet mycelium are treated with 6 l acetonitrile and stirred overnight. To the solution obtained after filtration, water is added to achieve approximately 50% organic solvent. The solution is then loaded on 10 l of phenolic resin XAD 761®. The elution is carried out with a water:acetonitrile gradient mixture ranging from 50:50 to 40:60.

A fraction containing cyclosporin C is collected followed by a mixture of the three cyclosporins C, B, and A, and then by a fraction containing only cyclosporin A which is recovered as in the Example 12.

EXAMPLE 14

Approximately 4 kg of wet mycelium is treated with 6 l of tetrahydrofuran and stirred for at least two hours at 35°-40° C. after which time, the suspension is filtered and the filter cake is washed with the same solvent. The aqueous organic solution is concentrated to bring the percentage of water to 60%. The solution so obtained is loaded into a column containing 9 l AMBERLITE XAD1600® resin that adsorbs the mixture of cyclosporins.

The cyclosporin elution is then carried out using a water::tetrahydrofuran gradient mixture ranging from 50:50 to 30:70. A fraction containing a mixture of cyclosporins C, B, and A is discarded while a fraction containing cyclosporins B and A is collected. To this fraction sufficient water is added to achieve a water:tetrahydrofuran ratio of 60:40. The solution so obtained is loaded into the same column for a second chromatographic purification, which is carried out in the same manner as the first.

A fraction containing a mixture of cyclosporins B and A is recycled in a successive chromatography while a fraction containing cyclosporin A is concentrated to recover the crude product that is crystallized with acetone.

EXAMPLE 15

Approximately 4 kg of wet mycelium is treated with 4 l dimethylformamide and stirred for about two hours at 50° C. After filtering sufficient water is added to achieve a water:DMF ratio of about 70:30. The solution is then loaded into a column containing 9 l adsorption resin XAD1600® to adsorb the mixture of cyclosporins. By elution with DMF:water gradient mixture varying from 70:30 to 50:50 is possible to obtain a fraction containing cyclosporin A accompanied by small percentage of cyclosporin B.

The foregoing is illustrative of the present invention and is not to be construed as limiting thereof. The invention is defined by the following claims, with equivalents of the claims to be included therein.

What is claimed is:

1. A method for isolating a cyclosporin by adsorption chromatography, said method comprising the steps of:
    (a) loading a crude solution containing a mixture of cyclosporin and compounds to be separated therefrom onto an adsorption chromatography column, said column containing an adsorption resin that adsorbs both said cyclosporin and said other compounds to be separated therefrom; then
    (b) eluting said cyclosporin from said adsorption chromatography column by passing an eluting solvent therethrough, wherein said cyclosporin is separately eluted from said other compounds by providing a hydrophilic/lipophilic balance in said eluting solvent that selectively desorbs said cyclosporin from said adsorption resin to provide an eluted cyclosporin essentially free of said compounds to be separated therefrom; and wherein said hydrophilic/lipophilic balance is provided by varying the ratio of a hydrophilic component to a lipophilic component in said eluting solvent during said eluting step; and then
    (c) collecting said eluted cyclosporin.

2. The method according to claim 1, wherein said crude solution comprises a mixture containing a cyclosporin and fermentation by-products and impurities.

3. The method according to claim 1, wherein said step (a) of loading comprises introducing onto said adsorption chromatography column, a solution comprising said crude solution and a loading solvent, said loading solvent comprising a hydrophilic component and a lipophilic component, wherein said loading solvent has a hydrophilic/lipophilic balance such that said cyclosporin preferentially adsorbs onto said adsorption resin.

4. The method according to claim 3, wherein said loading solvent comprises said hydrophilic component and said lipophilic component in a ratio of between about 70:30 to about 0:100.

5. The method according to claim 3, wherein said hydrophilic component of said loading solvent is selected from the group consisting of water and saline, and said lipophilic component of said loading solvent is selected from the group consisting of aliphatic alcohols, ketones, ethers, esters, amides, nitriles, and mixtures thereof.

6. The method according to claim 1, wherein said adsorption resin is an ionic or non-ionic adsorption resin.

7. The method according to claim 1, wherein said adsorption resin is selected from the group consisting of acrylic, methacrylic, styrenic, and phenolic adsorption resins.

8. The method according to claim 1, wherein said hydrophilic component of said eluting solvent is selected from the group consisting of water and saline and said lipophilic component of said eluting solvent is selected from the group consisting of aliphatic alcohols, ketones, ethers, esters, amides, nitriles, and mixtures thereof.

9. The method according to claim 1, wherein said ratio of hydrophilic component to lipophilic component in said eluting solvent is between about 90:10 and about 0:100 at the initiation of said step (b) of eluting said cyclosporin and is between about 0:100 and about 90:10 at the end of said step (b) of eluting said cyclosporin.

10. The method according to claim 1, wherein said ratio of hydrophilic component to lipophilic component in said eluting solvent is about 40:60 at the initiation of said step (b) of eluting said cyclosporin and is about 20:80 at the end of said step (b) of eluting said cyclosporin.

11. The method according to claim 1, wherein said step (c) of collecting said separately eluted cyclosporin comprises collecting an eluant fraction corresponding to said cyclosporin.

12. The method according to claim 1, further comprising the step (d) of purifying said collected cyclosporin by crystallization to yield substantially pure cyclosporin powder.

13. The method according to claim 1, further comprising the step of microfiltering a biomass containing said cyclosporin, fermentation broth, fermentation microorganism residues, lysed cells, and other fermentation compounds, prior to said step (a) of loading said crude solution onto said adsorption chromatography column.

14. A method of isolating a cyclosporin by adsorption chromatography, said method comprising the steps of:
 (a) loading a crude solution containing a mixture of at least two different cyclosporins to be separated onto an adsorption chromatography column, said column containing an adsorption resin that adsorbs each of said different cyclosporins;
 (b) eluting each of said individual cyclosporins from said adsorption chromatography column by passing an eluting solvent therethrough, wherein each of said individual cyclosporins are separately eluted from said column by providing a hydrophilic/lipophilic balance in said eluting solvent that selectively desorbs each of said individual cyclosporins from said adsorption resin to provide separately eluted individual cyclosporins essentially free of different cyclosporins, and wherein said hydrophilic/lipophilic balance is provided by varying the ratio of a hydrophilic component to a lipophilic component in said eluting solvent during said step of eluting; and then
 (c) collecting each of said separately eluted individual cyclosporins.

15. The method according to claim 14, wherein said crude solution comprises a mixture containing cyclosporins selected from the group consisting of cyclosporin A, cyclosporin B, cyclosporin C, cyclosporin D, cyclosporin E, cyclosporin F, and cyclosporin G.

16. The method according to claim 14, wherein said step (a) of loading comprises introducing onto said adsorption chromatography column, a solution comprising said crude solution and a loading solvent, said loading solvent comprising a hydrophilic component and a lipophilic component, wherein said loading solvent has a hydrophilic/lipophilic balance such that each of said cyclosporins preferentially adsorb onto said adsorption resin.

17. The method according to claim 16, wherein said loading solvent comprises said hydrophilic component and said lipophilic component in a ratio of between about 70:30 to about 0:100.

18. The method according to claim 16, wherein said hydrophilic component of said loading solvent is selected from the group consisting of water and saline, and said lipophilic component of said loading solvent is selected from the group consisting of aliphatic alcohols, ketones, ethers, esters, amides, nitriles, and mixtures thereof.

19. The method according to claim 14, wherein said adsorption resin is an ionic or non-ionic adsorption resin.

20. The method according to claim 14, wherein said adsorption resin is selected from the group consisting of acrylic, methacrylic, styrenic, and phenolic adsorption resins.

21. The method according to claim 14, wherein said hydrophilic component of said eluting solvent is selected from the group consisting of water and saline and said lipophilic component of said eluting solvent is selected from the group consisting of aliphatic alcohols, ketones, ethers, esters, amides, nitriles, and mixtures thereof.

22. The method according to claim 14, wherein said ratio of hydrophilic component to lipophilic component in said eluting solvent is between about 90:10 and about 0:100 at the initiation of said step (b) of eluting said cyclosporin and is between about 0:100 and about 90:10 at the end of said step (b) of eluting said cyclosporin.

23. The method according to claim 14, wherein said ratio of hydrophilic component to lipophilic component of said eluting solvent is about 40:60 at the initiation of said step (b) of eluting said cyclosporin and is about 20:80 at the end of said step (b) of eluting said cyclosporin.

24. The method according to claim 14, wherein said step (c) of collecting comprises separately collecting chant fractions corresponding to each of said individual cyclosporins.

25. The method according to claim 14, further comprising the step (d) of purifying said collected cyclosporin by crystallization to yield substantially pure cyclosporin powder.

26. The method according to claim 14, further comprising the step of microfiltering a biomass containing said cyclosporin, fermentation broth, fermentation microorganism residues, lysed cells, and other fermentation compounds, prior to said step (a) of loading.

27. A method for isolating a cyclosporin by adsoprtion chromatography, said method comprising the steps of:
 (a) lysing cells containing intracellular cyclosporin with a lysis solution comprising a lysis solvent selected from the group consisting of ketones, ethers, esters, amides, nitriles, and mixtures thereof, to produce lysed cells;
 (b) microfiltering said lysed cells to separate cellular debris and to produce a crude solution comprising cyclosporin and compounds to be separated therefrom;
 (c) loading said crude solution onto an adsorption chromatography column, said column containing an adsorption resin that adsorbs both said cyclosporin and said other compounds to be separated therefrom; then
 (d) eluting said cyclosporin from said adsorption chromatography column by passing an eluting solvent therethrough, wherein said cyclosporin is separately eluted from said other compounds by providing a hydrophilic/lipophilic balance in said eluting solvent that selectively desorbs said cyclosporin from said adsorption resin to provide an eluted cyclosporin essentially free of said compounds to be separated therefrom; and wherein said hydrophilic/lipophilic balance of said eluting solvent is provided by varying the ratio of a hydrophilic component to a lipophilic component in said eluting solvent during said eluting step; and then (e) collecting said eluted cyclosporin.

28. The method according to claim 27, wherein said lipophilic component of said eluting solvent is selected from the group consisting of aliphatic alcohols, ketones, ethers, esters, amides, nitriles, and mixtures thereof.

29. The method according to claim 27, wherein said lysis solvent and said lipophilic component are the same.

30. The method according to claim 27, wherein said step (a) of loading comprises introducing onto said adsorption chromatography column, a solution comprising said crude solution and a loading solvent, said loading solvent comprising a hydrophilic component and a lipophilic component, wherein said loading solvent has a hydrophilic/lipophilic balance such that said cyclosporin preferentially adsorbs onto said adsoprtion resin.

31. The method according to claim 30, wherein said lysis solvent, said lipophilic component of said loading solvent and said lipophilic component of said eluting solvent are the same.

32. The method according to claim 31, wherein said lysis solvent, said lipophilic component of said loading solvent and said lipophilic component of said eluting solvent are acetone.

33. A method for isolating a cyclosporin by adsoprtion chromatography, said method comprising the steps of:

(a) lysing cells containing intracellular cyclosporin with a lysis solution comprising a lysis solvent selected from the group consisting of ketones, ethers, esters, amides, nitriles, and mixtures thereof, to produce lysed cells;

(b) microfiltering said lysed cells to separate cellular debris and to produce a crude solution comprising a mixture of at least two different cyclosporins to be separated;

(c) loading said crude solution onto an adsorption chromatography column, said column containing an adsorption resin that adsorbs each of said different cyclosporins; then (d) eluting each of said individual cyclosporins from said adsorption chromatography column by passing an eluting solvent therethrough, wherein each of said cyclosporins are separately eluted from said column by providing a hydrophilic/lipophilic balance in said eluting solvent that selectively desorbs each of said individual cyclosporins from said adsorption resin to provide separately eluted individual cyclosporins essentially free of different cyclosporins, and wherein said hydrophilic/lipophilic balance of said eluting solvent is provided by varying the ratio of a hydrophilic component to a lipophilic component in said eluting solvent during said eluting step; and then (e) collecting each of said separately eluted individual cyclosporins.

34. The method according to claim 33, wherein said lipophilic component of said eluting solvent is selected from the group consisting of aliphatic alcohols, ketones, ethers, esters, amides, nitriles, and mixtures thereof.

35. The method according to claim 33, wherein said lysis solvent and said lipophilic component are the same.

36. The method according to claim 33, wherein said step (a) of loading comprises introducing onto said adsorption chromatography column, a solution comprising said crude solution and a loading solvent, said loading solvent comprising a hydrophilic component and a lipophilic component, wherein said loading solvent has a hydrophilic/lipophilic balance such that each of said cyclosporins preferentially adsorbs onto said adsoprtion resin.

37. The method according to claim 36, wherein said lysis solvent, said lipophilic component of said loading solvent and said lipophilic component of said eluting solvent are the same.

38. The method according to claim 37, wherein said lysis solvent, said lipophilic component of said loading solvent and said lipophilic component of said eluting solvent are acetone.

39. A method for isolating cyclosporin A from a mixture by adsorption chromatography, said method comprising the steps of:

(a) loading a crude solution containing cyclosporin A and compounds to be separated therefrom onto an adsorption chromatography column, said column containing a adsorption resin that both adsorbs said cyclosporin A and said compounds to be separated therefrom; then (b) separately eluting said cyclosporin A from said adsorption chromatography column by passing an eluting solvent therethrough, said eluting solvent comprising water and acetone, wherein said cyclosporin A is separately eluted from said column by providing a water/acetone balance in said eluting solvent that selectively desorbs said cyclosporin A from said adsorption resin to provide eluted cyclosporin A essentially free of said compounds to be separated therefrom;

and wherein said water/acetone balance is provided by varying the ratio of water to acetone in said eluting solvent from about 50:50 at the initiation of said step (b) of separately eluting said cyclosporin A, to about 20:80 at the end of said step (b) of separately eluting said cyclosporin A; then (c) collecting said eluted cyclosporin A.

40. The method according to claim 39, further comprising the step (d) of purifying said collected cyclosporin A by crystallization to yield substantially pure cyclosporin A powder.

41. A method for isolating cyclosporin A from a mixture by adsorption chromatography, said method comprising the steps of:

(a) lysing cells containing intracellular cyclosporin A with a lysis solution-comprising acetone to produce lysed cells;

(b) microfiltering said lysed cells to separate cellular debris and to produce a crude solution comprising cyclosporin A;

(c) loading said crude solution containing cyclosporin A and compounds to be separated therefrom onto an adsorption chromatography column, said column containing a adsorption resin that both adsorbs said cyclosporin A and said compounds to be separated therefrom; then (d) separately eluting said cyclosporin A from said adsorption chromatography column by passing an eluting solvent therethrough, said eluting solvent comprising water and acetone, wherein said cyclosporin A is separately eluted from said column by providing a water/acetone balance in said eluting solvent that selectively desorbs said cyclosporin A from said adsorption resin to provide eluted cyclosporin A essentially free of said compounds to be separated therefrom;

and wherein said water/acetone balance is provided by varying the ratio of water to acetone in said eluting solvent from about 50:50 at the initiation of said step (c) of separately eluting said cyclosporin A, to about 20:80 at the end of said step (c) of separately eluting said cyclosporin A; then (e) collecting said eluted cyclosporin A.

42. The method according to claim 41, further comprising the step (f) of purifying said collected cyclosporin A by crystallization to yield substantially pure cyclosporin A powder.

* * * * *